US006035047A

United States Patent [19]

Lewis

[11] Patent Number: 6,035,047

[45] Date of Patent: Mar. 7, 2000

[54] SYSTEM TO BLOCK UNWANTED SOUND WAVES AND ALERT WHILE SLEEPING

[76] Inventor: Mark Henry Lewis, Watts Post Office, 10301 S. Compton Ave., Los Angeles, Calif. 90002-9998

[21] Appl. No.: 08/851,640

[22] Filed: May 6, 1997

Related U.S. Application Data

[60] Provisional application No. 60/017,383, May 8, 1996.

[51] Int. Cl.[7] ........................................ A61F 11/06

[52] U.S. Cl. ........................ 381/72; 381/74; 367/197; 340/825.19

[58] Field of Search ........................ 381/72, 74, 311, 381/300; 367/197, 199; 340/825.19, 407.1, 965

[56] References Cited

U.S. PATENT DOCUMENTS

| | | | |
|---|---|---|---|
| 3,530,509 | 9/1970 | Simpson et al. . | |
| 3,539,031 | 11/1970 | Scanlon . | |
| 4,047,377 | 9/1977 | Banks . | |
| 4,654,871 | 3/1987 | Chapin et al. . | |
| 4,682,159 | 7/1987 | Davison | 340/825.19 |
| 5,287,102 | 2/1994 | McKiel | 340/825.19 |
| 5,309,145 | 5/1994 | Branch et al. . | |
| 5,508,699 | 4/1996 | Silverman | 340/825.19 |

OTHER PUBLICATIONS

NoiseBuster Active Noise–Reduction Headset from Noise Cancellation Technologies at 800 Summer St., Stamford, CT 06901.

Discwasher Model NC200 Noise Cancellation Headphone by Recoton at 145 East 57th St., New York, NY 10022.

*Primary Examiner*—Minsun Oh Harvey

[57] ABSTRACT

A cordless, wireless headset to block unwanted sound waves and/or noise from entering the ears of a user. The headset (FIG. 5) contains an electronic receiver, an audible tone/alert generator, volume control/switch and battery. The wireless headset would permit freedom of movement during sleep without danger of being entangled by cords/wires. The wireless headset would be secured to the ears and head of the user while sleeping by a Top head-strap, a Rear head-strap and Chin-strap. Referencing FIG. 1, the wireless headset will receive and interpret signals from remote sound sensor (s) and/or motion detection sensor(s). Remote sensor(s) would transmit radio signal(s) to the headset when an unwanted sound or motion is detected. The signal would be received in the wireless headset and an audible tone would be generated in the ear of the user, to alert of an important event.

6 Claims, 9 Drawing Sheets

SYSTEM TO BLOCK UNWANTED SOUND WAVES AND ALERT WHILE SLEEPING

This application claims benefit of provisional application Ser. No. 60/017,383 filed May 8, 1999.

BACKGROUND—FIELD OF INVENTION

This invention relates to the blockage of unwanted sounds and/or noise from entering a person's ears, while at the same time allowing that person to be alerted of, or notified of, important emergency sounds and noises (such as fire or burglar alarms) and/or intrusions.

BACKGROUND—DESCRIPTION OF PRIOR ART

There are several types of devices which try to stop, prevent, block or dampen external unwanted sounds and/or noises from entering the ear of a person or user of a particular device. Some devices are designed to dampen or stop unwanted sounds to help a person sleep better. U.S. Pat. No. 4,047,377(Sleep-Inducing/Interrupting Audio System) granted Sep. 13, 1977 shows a system which is physically hard-wired to the earphones and physically connects to an external house system such as a burglar alarm or smoke alarm; however, this system will not permit undisturbed sleep. It will not permit undisturbed sleep because the user must be conscious and aware to not become entangled in the physical wires connected to the earphones. U.S. Pat. No. 5,309,145 (Travel Convenience and Security device) granted May 3, 1994 discloses a complex system which does not prevent noise or unwanted sounds from entering the a persons ear; thus, it is not effective in helping a person to sleep.

Noise Cancellation Technologies Inc., of Stamford, Conn. produces a product called the Noisebuster headphone; and also Discwasher, a division of Recoton of New York, N.Y. both produce headphones that utilize electronic noise cancellation to prevent unwanted sounds from entering a persons ear; however, the headphones of these devices are physically connected using wires from the headphones to the noise cancellation electronics. The physical wires to the headphones will not permit undisturbed sleep because the user must be conscious and aware to not become entangled in the physical wires connected to the headphones during natural movements. Also these products will not alert the user of important or desired sounds and/or noises that may warn the user of potential danger or harm, or alert the user of physical intrusions while sleeping.

Conventional ear-plugs designed to prevent unwanted sounds from entering the ear while sleeping or concentrating do not alert the user of important sounds and/or noises that may warn the user of potential danger or harm. The user of ear-plugs will also not be alerted of physical intrusions while sleeping.

OBJECTS AND ADVANTAGES

There are several objects and advantages of this System To Block Unwanted Sound Waves And Alert While Sleeping invention. The System would stop, prevent, block and/or dampen most unwanted sounds and/or noises from entering a persons or the users ear when sleeping, resting, reading, studying or meditating. While the user is sleeping the System would alert the user of important or emergency sounds (such as sounds made by a smoke alarm, fire alarm, burglar alarm, telephone or pager). The System would also alert the user of intrusions by another person through the incorporation of an infrared motion detector. With this System the user will not have to relocate to locations within his or her home or city to escape unwanted sounds for sleeping purposes or for peace of mind.

The System To Block Unwanted Sound Waves And Alert While Sleeping will permit or allow for uninterrupted sleep because it consists of a cordless (or wireless) headset which would block unwanted sounds from entering the ears of the user, an internal audible tone/alert generator and a radio frequency receiver which eliminates the need to have the headset physically connected or hardwired to the radio transmitter of the sound sensor(s) and/or motion detector. Elimination of the physical wires externally connected to the headset would permit uninterrupted sleep because the user would not need to be conscious of wires which could entangle the user, during natural movements, and disrupt sleep. The wireless headset would allow and permit freedom of movement during sleep without the inconvenience of being tangled by wires. The audible alarm and receiver electronics within the headset will alert the user of important sounds or intrusions given a radio signal transmitted from remote sound and/or motion detectors.

The System offers advantages over conventional ear-plugs by blocking unwanted sounds which would aid the users sleep and/or concentration and alert the user of important sounds or intrusions. The wire-less headset of the System consists of several straps that would secure the two sound blocking ear covers of the headset to the head of the user which would permit the user to move or reposition his head while sleeping without displacing or dislodging the headset.

Further objects and advantages of this System will become apparent from a consideration of the drawings/illustrations and ensuing description.

DRAWING FIGURES

FIG. 1 shows a flow chart of the logical operation of the System To Block Unwanted Sound Waves And Alert While Sleeping.

FIG. 2 shows a schematic diagram illustrating one possible embodiment of the sound activated radio transmitter.

FIG. 3 shows a schematic diagram illustrating one possible embodiment of the infrared motion detection activated transmitter.

FIG. 4 shows a schematic diagram illustrating one possible embodiment of the radio receiver and alert/tone generator electronics.

FIG. 5 shows a diagram illustrating one embodiment of the wireless/cordless headset containing the schematic diagram of FIG. 4.

FIG. 6 shows a diagram representing one possible application of the System To Block Unwanted Sound Waves And Alert While Sleeping.

SUMMARY

The System consists of a cordless (or wireless) headset which is made to block unwanted sound waves and/or noise from entering the ears of the user. The headset (FIG. 5) would contain an electronic radio receiver, an audible tone/alert generator, volume control/switch and 9 volt battery. The wireless headset would allow and permit freedom of movement during sleep without the inconvenience of being entangled by wires or cords. The wireless headset would incorporate a Top head-strap, a Rear head-strap and a Chin-strap, to secure the headset to the users ears and head while sleeping. With traditional electronic headphones there are wires attached to earphones which could entangle the user during natural movements while sleeping. Referencing the diagram of FIG. 1, the wireless headset will receive and interpret transmitted signals from remote sound sensor(s) and/or motion detection sensor(s). When an important sound or intruder motion is detected by the remote sensors a signal will be transmitted from the remote sensor(s) to the receiver in the wireless headset. The wireless headset will then generate an audible tone, in the ear of the user, to alert the user that something important may be happening.

The brief summary above was given for purposes of cursive description and not as limitation.

BRIEF DESCRIPTION OF THE DRAWINGS

The remote sound sensor is shown in FIG. 2. The MIC-1 senses a sound waveform and couples it to the base of transistor Q1 by a capacitor C1. Q1 is configured as a common emitter amplifier since the AC signal is by-passed to ground by capacitor C2. The sound waveform is amplified by Q1. Capacitor C3 couples the amplified waveform to the input of the first digital circuit. The potentiometer, P1, adjusts the sensitivity of the Sound Activated Switch. Varying the resistance of P1 will vary the DC voltage at the input of the NAND digital circuit N1. Rotating P1 counter clockwise causes the voltage at the input of N1 to increase. This means that a louder sound or noise is required to activate N1, making the Sound Activated Switch less sensitive to a sound or noise wave. Rotating P1 clockwise causes the voltage at the input of N1 to decrease. This means that the Sound Activated Switch is more sensitive to sound waves. The N1 circuit will switch its output levels when the input is triggered. When the input to N1 goes low, due to a sound wave, the output of N1 changes from a low voltage, logic 0, to a high voltage logic 1.

The output of N1 provides a current to the base of transistor Q2. Resistor R16 sets the current through the base of Q2. This base current turns on Q2 causing current to flow through the LED (D1) and R17. D1 will emit light when current flows through it. R17 is used to limit the current through D1 so that D1 is not damaged. D1 is also a way to determine the operation of the Sound Activated Switch. The switch SW0 will disable the 9 volt battery thus turning the Sound Activated Switch and Transmitter of FIG. 2 off. Relay1, is used to drive the inputs (pins 5 and 6) of IC1. IC1 is a National Semiconductor LM1871 chip, intended for use as a low power, license-free, non-voice communications device for use on 27 or 49 MHz. When the inputs of IC1 are driven to ground by Relay1, IC1 will transmit a waveform which will be received and interpreted by the Receiver (located in the wireless headset), IC2 in FIG. 4. The two digital receiver outputs are determined by the number of pulses transmitted. Two timing circuits make up the transmitter's encoder. Frame time is determined by the values of R5T and C9T at pin 7 of IC1; pulse time at pin 8 is determined by the values of C7T and R4T. Frame time (R5TC9T+0.63R4TC7T), modulation time (0.63R4TC7T), and channel time (0.63R3TC7T) which in this configuration are set for 9.5, 0.5 and 0.5 milliseconds, respectively. Class C was chosen as the operating mode for the crystal controlled oscillator/transmitter. Resistor R2T provides base bias current from pin 4 of IC1. R-f feedback in the oscillator is via series-mode third-overtone crystal XTAL1, which controls the frequency of oscillation. L1 is tuned for minimum supply current (observing the carrier envelope) which is the best alignment method. The digital channels in this System use a form of pulse position modulation. The analog portion of IC1 is not used and is thus disabled. The generated waveform is delivered through the transmitter's antenna to the antenna of the receiver in the wireless headset. The sound sensor would be located within the effective range of the transmitter and receiver electronics.

The remote motion detector is sketched in FIG. 3. As motion is detected, the PIR infrared detector will produce a voltage at the input of the N2. The resistors R1M and R2M limit the amount of current flow through the PIR. C1M and C6M provide isolation from ground. The output of N2 is changed, from a logic 1, to a logic 0. The output of N2 provides the input to IC1Z of the transmitter in FIG. 3.

Figure 1:
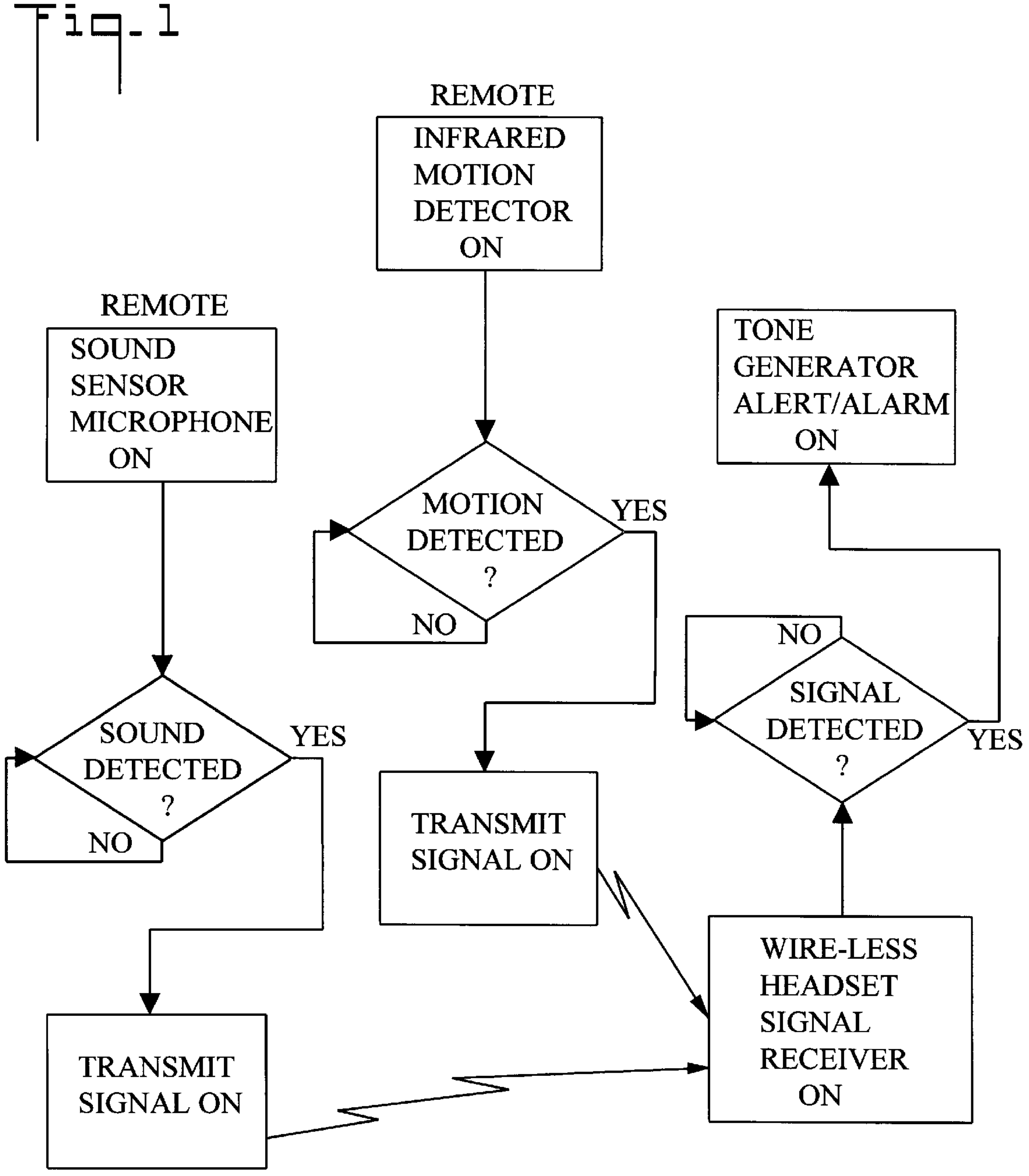
Figure 2A:
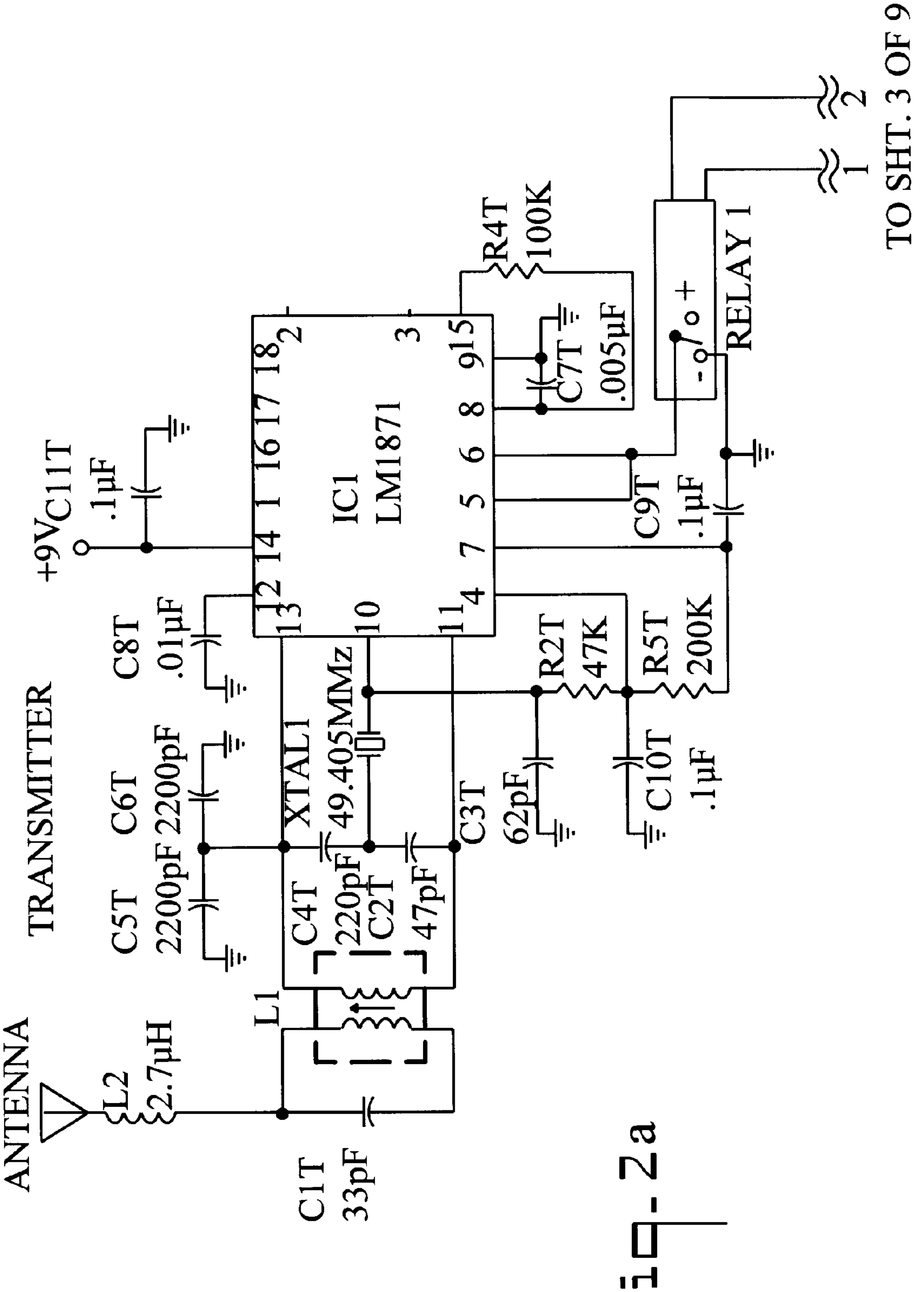
Figure 2B:
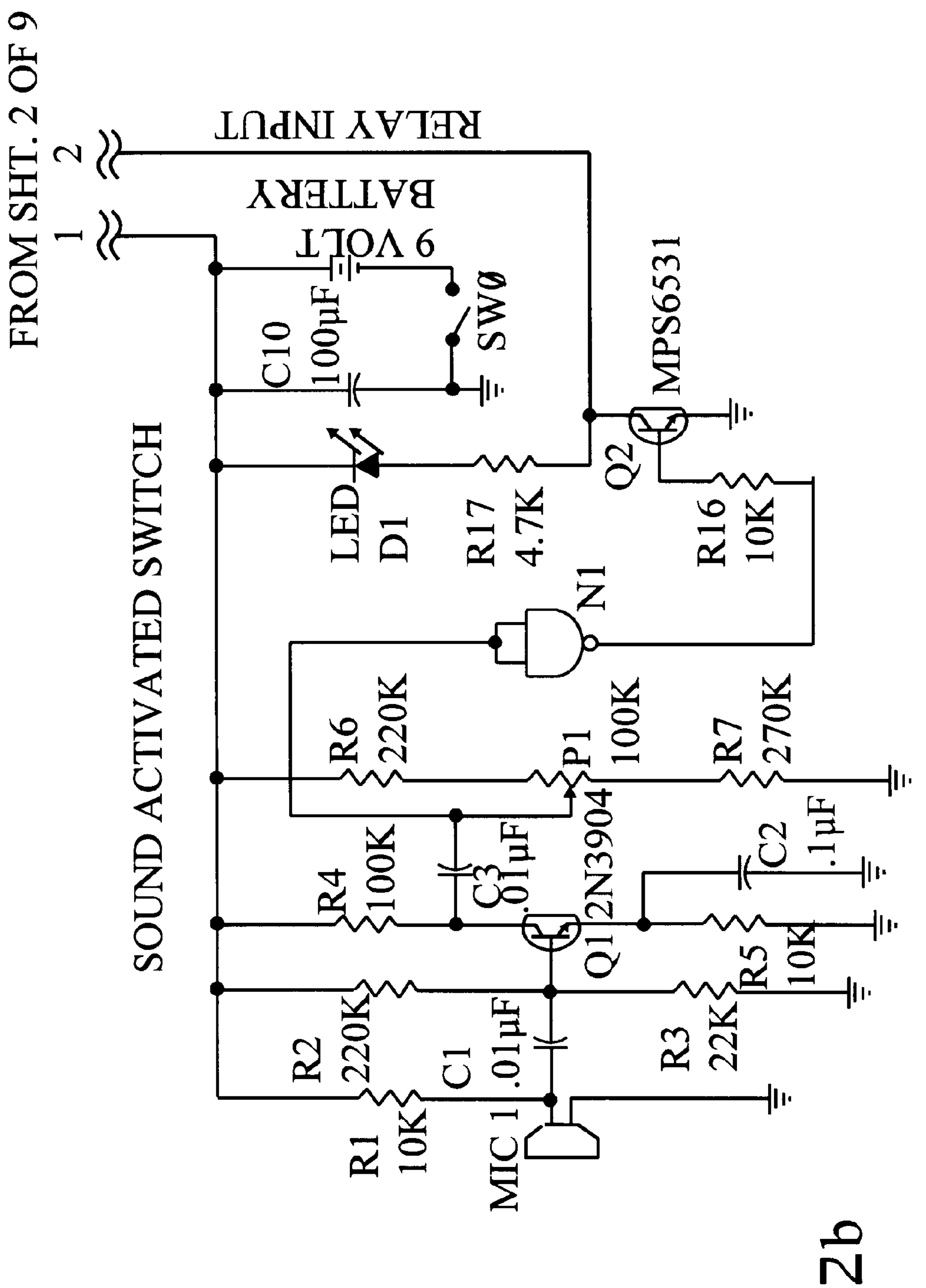
Figure 3A:
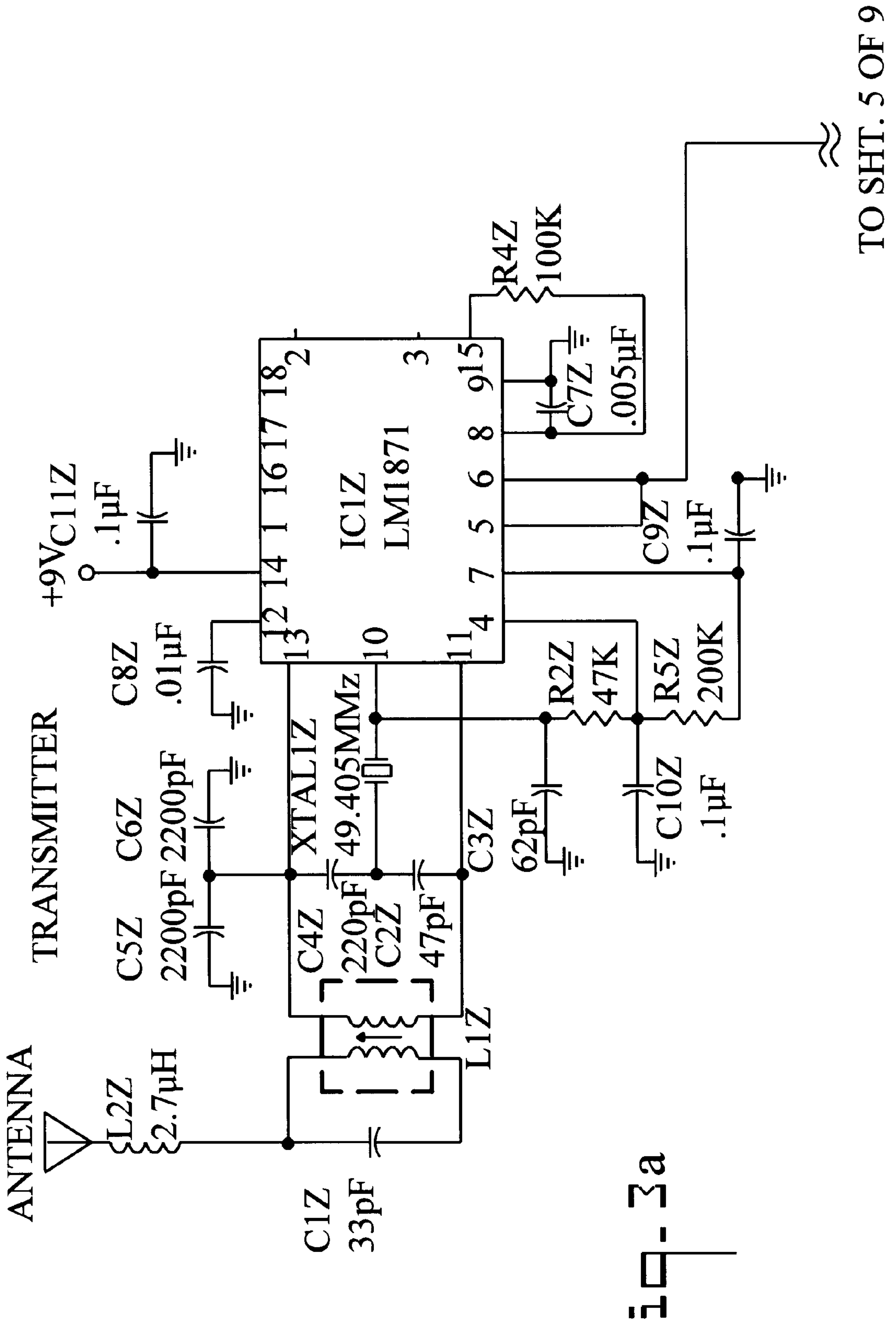
FIG. 3 also contains IC3 which converts 9 battery volts to 5 volts (VCC) for use by the PIR. SW3 can be used to disable the battery and thus turn-off the motion detector and transmitter in FIG. 3. IC1Z is also a National Semiconductor LM1871 chip. When the inputs (pins 5 and 6) of IC1Z are driven to ground by N2, IC1Z will transmit a waveform which will be received and interpreted by the wireless headset electronic receiver, IC2 in FIG. 4. The two digital receiver outputs are determined by the number of pulses transmitted. Two timing circuits make up the transmitter's encoder. Frame time is determined by the values of R5Z and C9Z at pin 7 of IC1Z; pulse time at pin 8 is determined by the values of C7Z and R4Z. Frame, modulation and channel times are set for 9.5, 0.5 and 0.5 milliseconds, respectively in this particular configuration. Class C was chosen as the operating mode for the crystal controlled oscillator/transmitter. Resistor R2Z provides base bias current from pin 4 of IC1Z. R-f feedback in the oscillator is via series-mode third-overtone crystal XTAL1Z, which controls the frequency of oscillation. L1Z is tuned for minimum supply current. The analog portion of IC1Z is disabled. The generated waveform is delivered through the transmitter's antenna to the antenna of the receiver in the wireless headset. The infrared motion sensor would be located within the effective range of the transmitter and receiver electronics.
Figure 3B:
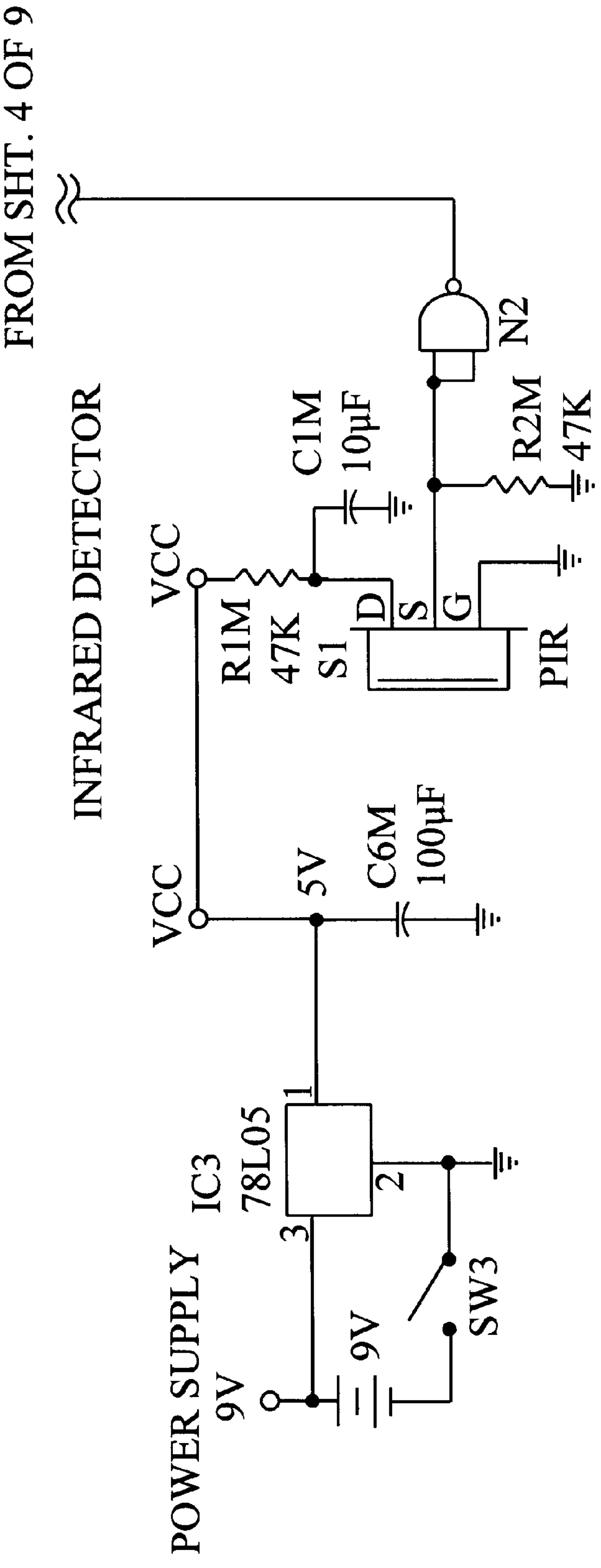
Figure 4A:
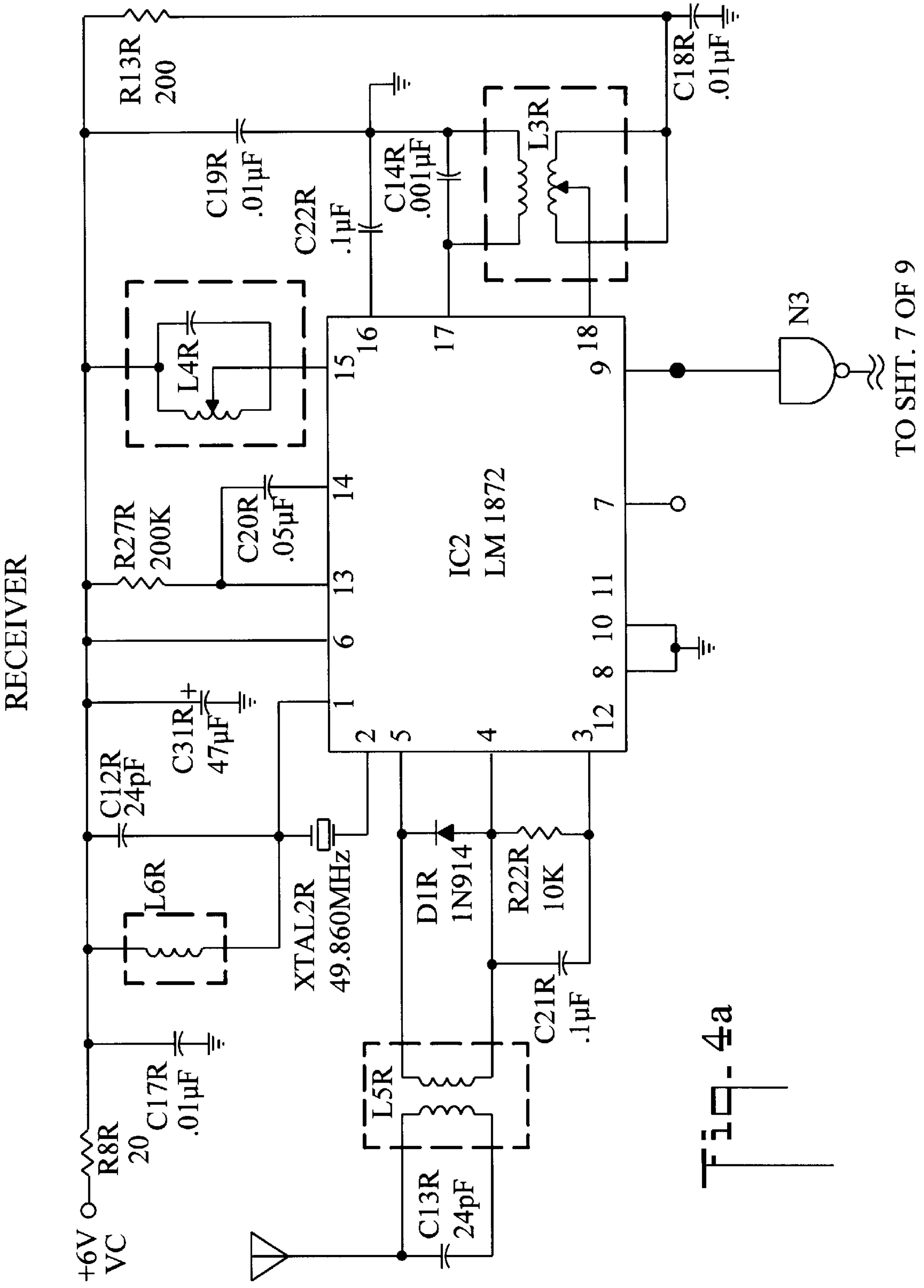
Figure 4B:
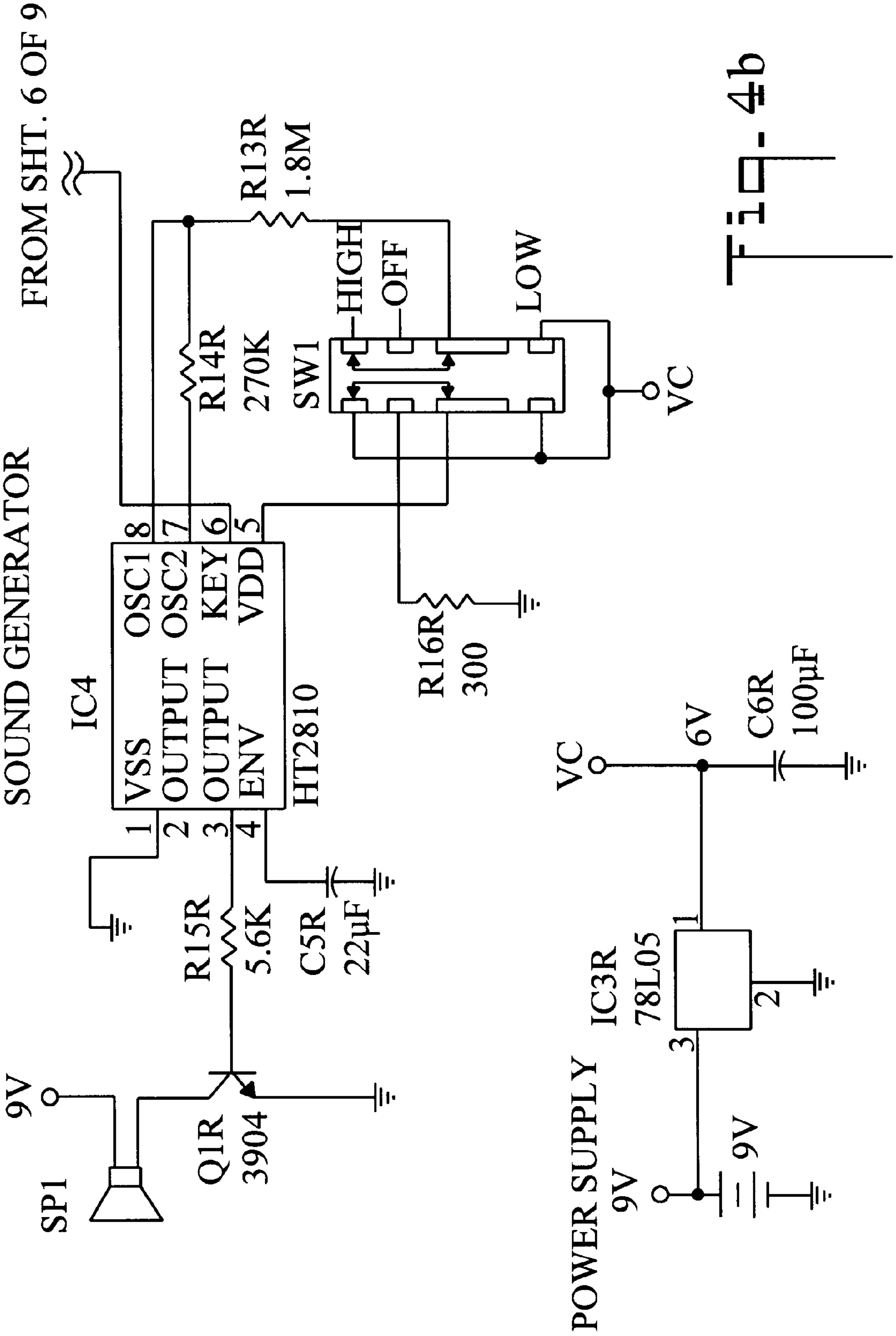

The wireless headset receiver and tone generator electronics are shown in FIG. 4. The receiver (IC2) is based on National Semiconductor's, license free, LM1872 radio-control receiver/decoder chip. The R-f signal from the remote transmitter(s) is detected by the receiver and converted into pulses. The L5R/C13R input circuit prevents strong out-of-band TV and FM signals from cross-modulating the desired signal. The pulses are counted and decoded to switch the digital outputs of the receiver to a logic 1.

The logic 1 at the output of the IC2 receiver is input to N3. The output of N3 changes to a logic 0. The output of N3 is connected to pin 6 of IC4. As pin 6 of IC4 is brought low, IC4 is enabled, which generates an output frequency at IC4 pin 3. Switch SW1 has three positions: Low/High/Off. When set to Low, SW1 connects R13R from pin 8 to VC (6-volts). This decreases the voltage to pin 8, thus decreasing the oscillator frequency generated by IC4 to 45 KHz. In the Off position VC is removed from IC4 pin 5 and switched to ground through R16R, disabling IC4. In the High position, VC is removed from R13R which reduces the voltage at IC4 pin 8, leaving R14R across pins 7 and 8 which sets the frequency to 65 KHz.

The output of IC4, in FIG. 4, is used to turn Q1R on and off. This allows current to flow from the collector to emitter. The output of IC4 consists of either two sequences of pulses. In this particular configuration, in the Low mode, IC4 outputs a series of pulses at 892 Hz then a series of pulses at 714 Hz (to generate a ding-dong sound alert). The High mode outputs a series of pulses at 1 KHz and a series at 961 Hz. To prevent over-driving Q1R, the resistor R15R is placed in series with the output of IC4 and the base of Q1R. Each time Q1R turns on a tone is generated from the miniature speaker SP1. The voltage level of IC4 pin 3 is ramped down by placing C5R from pin 4 to ground. As the voltage from pin 3 decreases, Q1R turns off slowly which causes the speaker's sound to decrease, contributing to a ding-dong sound effect. FIG. 4 also contains IC3R which converts 9 battery volts to 6 volts (VC) for use by the receiver and IC4.

Figure 5:
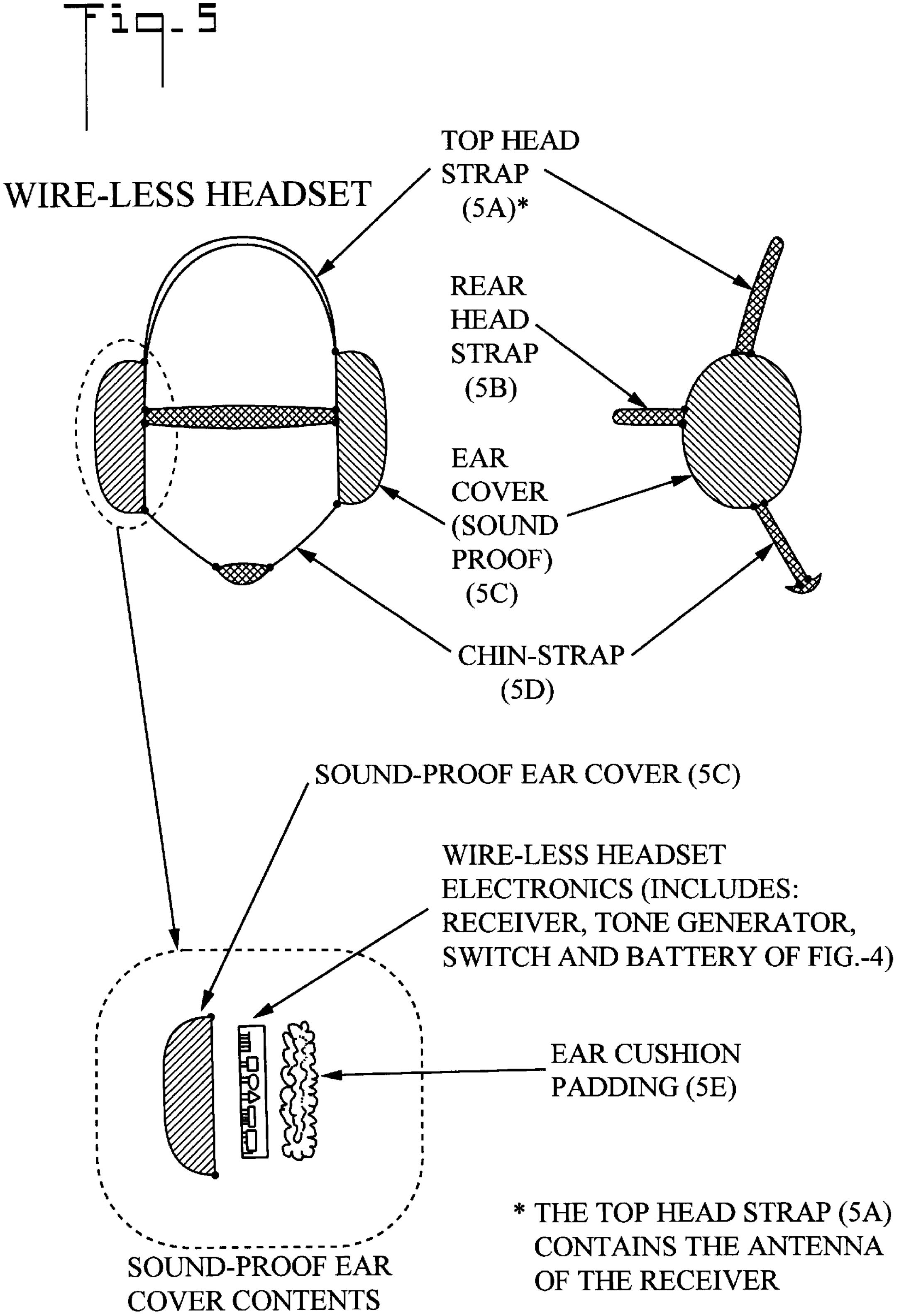

All of the receiver and tone generation electronics (shown in FIG. 4) resides in the wireless headset as illustrated in FIG. 5. The headset would consist of two ear covers (5C), made of sound proof material, designed to keep a high percentage of unwanted sound waves or noise from physically entering the ears of a person or user. Inside one of the two ear covers there are the miniature compact electronics of FIG. 4. Both ear covers contain padding materials (5E) to cushion the ear for comfortable wearing. The headset will be secured to the head of the user by the use of three adjustable straps. The Top head strap (5A) would attach to, and secure, the ear-covers from the top of the user's head. The Rear head strap (5B) would wrap around the back of the user's head and connect to each ear-cover. The Chin strap 5(D) would also attach to both ear-covers and provide a third axis of security for the ear covers of the headset. With the wireless headset secured the user could move (toss and/or turn) while sleeping on a bed, couch or chair and not get tangled in wires as with conventional audio headphones.

The receiver antenna (sketched in FIG. 4) would reside inside the Top head strap (5A) of the wireless headset. The receiver antenna would be a small plastic coated flexible copper wire at least 12 inches long.

Figure 6:
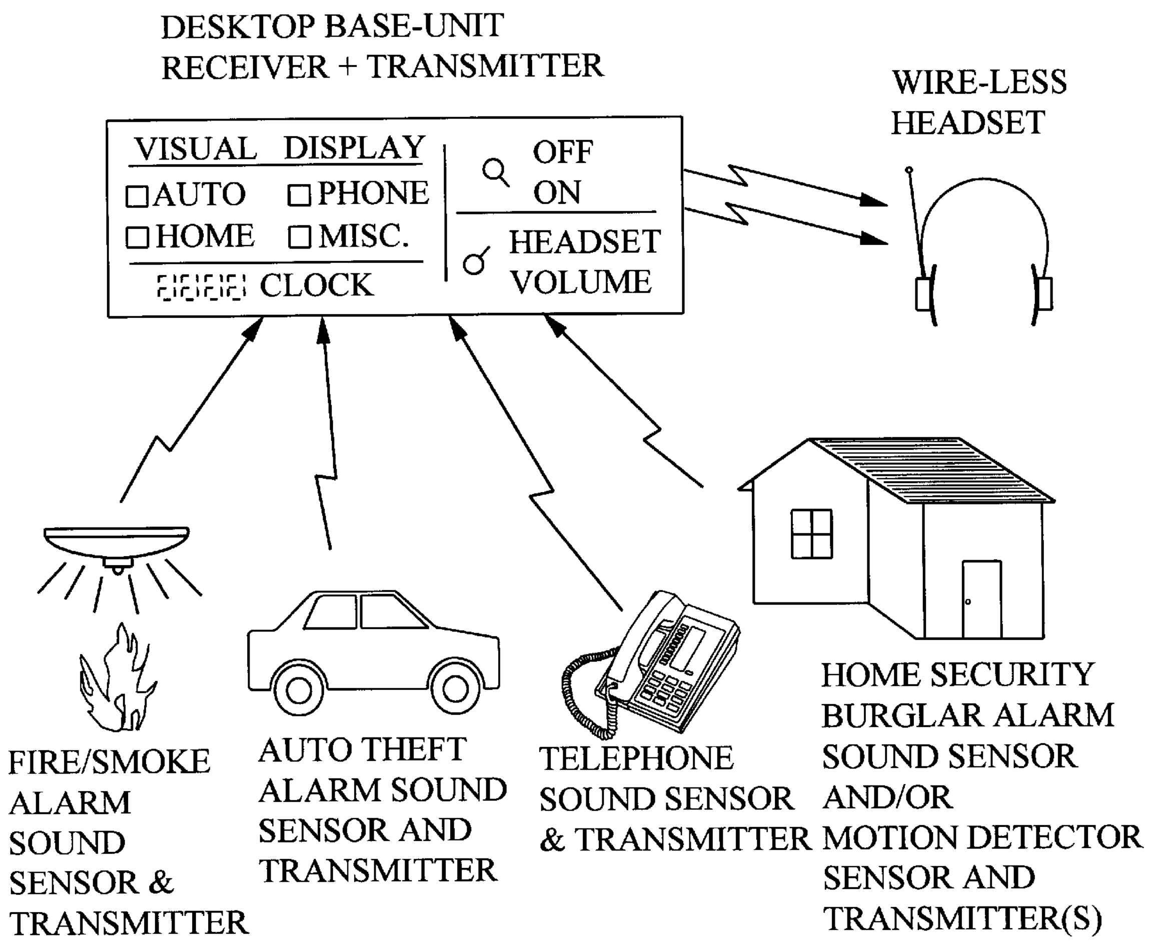

FIG. 6 illustrates one of many embodiments of this invention where several independent remote transmitters are utilized in different locations, in or near different devices which generate important sounds. A desktop base unit receiver would receive individual transmitted signal(s) sent from remote sensor(s) and then transmit a radio signal to the cordless/wireless headset. The headset would receive the signal from the desktop base unit and will then generate an audible tone, in the ear of the user, to alert the user that something important may be happening.

No claim is made to invention of any electronic subcomponents of this invention. There are different types of radio transmitters and receivers that are publicly and commercially well known and may be purchased or built which offer equal and/or enhanced function to transmitters (IC1 and IC1Z) and/or receiver (IC2) described and illustrated in this invention and which could be used in the place of illustrated embodiments or descriptions of transmitters and/or receivers in this invention.

Conclusions, Ramifications, and Scope

The reader will see that the sound control system of this invention can be used as an aid to obtain undisturbed sleep and at the same time be alerted of emergencies or other important events. Furthermore, this sound control system has additional advantages in that

- it physically blocks, prevents and/or dampens unwanted sounds and/or noises from entering a persons whiles sleeping;
- it permits secure placement over the ears of a user and would not be dislodged during natural movements of the user while sleeping;
- it assists uninterrupted sleep because it incorporates cordless (or wireless) radio receiver and transmitter technologies in the headset allowing freedom of movement without worry or danger of being entangled while sleeping or resting;
- it would alert the user of important or desired sounds (such as sounds made by a smoke alarm, fire alarm, burglar alarm, telephone or pager) when sleeping, resting, reading, studying, and/or meditating;
- it has the ability to alert the user of intrusions by another person through the incorporation of an infrared motion detector;
- it can be adjusted to a user selected sensitivity to permit only unwanted sounds of a certain decibel level to be detected;
- it is portable and can be carried with the user to remote locations.

While the above description contains many specifics, these should not be construed as limitations on the scope of the invention, but rather as an exemplifications of one preferred embodiment thereof. Many other variations are possible. For example the sound sensor transmitter could be incorporated directly into, or as part of, a specific important sound source instead of as a separate detached unit. A radio transmitter incorporated directly into an important sound source would transmit a signal to the headset receiver electronics and activate the tone generator and alert the wearer of the headset of the important sound in the same manner as described above in this System. The components of this invention can be miniaturized given advancements in micro-electronics.

Accordingly, the scope of this System should be determined by the appended claims and their legal equivalents, rather than by the embodiment(s), illustrations or examples given.

I claim:

1. A sound control system comprising:

a headset for placement over the ears of a user to block unwanted sounds;

said headset having an integral alert generator;

said headset having an integral receiver;

a selectively locatable sound sensor for sensing important sounds, said sound sensor having a first transmitter for transmitting a sound signal to said receiver; and, so that when said receiver receives said sound signal, said alert generator is activated.

2. A system according to claim 1, wherein said receiver and said sound sensor receive and transmit respectively by radio frequency.

3. A system according to claim 1, wherein said alert generator may be selectively enabled and disabled.

4. A system according to claim 1, further including;

a selectively locatable motion detector for detecting moving objects, said motion detector having a second transmitter for transmitting a motion signal to said receiver; and, so that when said receiver receives said motion signal, said alert generator is activated.

5. A system according to claim 4, wherein said receiver and said motion detector receive and transmit respectively by radio frequency.

6. A system according to claim 4, wherein said alert generator may be selectively enabled and disabled.

* * * * *

UNITED STATES PATENT AND TRADEMARK OFFICE
CERTIFICATE OF CORRECTION

PATENT NO. : 6,035,047
DATED : March 7, 2000
INVENTOR(S) : Mark Henry Lewis

It is certified that error appears in the above-identified patent and that said Letters Patent is hereby corrected as shown below:

[76] Inventors: Mark Henry Lewis
814 E. 94th Street
Los Angeles, CA 90002

Signed and Sealed this

Fifteenth Day of May, 2001

Attest:

*Nicholas P. Godici*

NICHOLAS P. GODICI

*Attesting Officer*

*Acting Director of the United States Patent and Trademark Office*